United States Patent [19]
Honkanen et al.

[11] Patent Number: 5,914,242
[45] Date of Patent: Jun. 22, 1999

[54] METHOD FOR DIMINISHING MYOCARDIAL INFARCTION USING PROTEIN PHOSPHATASE INHIBITORS

[75] Inventors: Richard Eric Honkanen; James M. Downey, both of Mobile, Ala.

[73] Assignee: South Alabama Medical Science Foundation, Mobile, Ala.

[21] Appl. No.: 08/941,964

[22] Filed: Oct. 1, 1997

Related U.S. Application Data

[60] Provisional application No. 60/027,809, Oct. 4, 1996.
[51] Int. Cl.$^6$ .............................. C12Q 1/00; G01N 33/53
[52] U.S. Cl. ......................... 435/7.71; 435/7.72; 435/184
[58] Field of Search .................................. 435/7.71, 7.72, 435/183, 184; 424/94.1, 94.64

[56] References Cited

PUBLICATIONS

R.S. de Jong, et al. Fostriecin: a Review of the Preclinical Data. Anti–Cancer Drugs 1997, vol. 8, pp. 413–418 (1997).
X.W. Guo, et al. Chromosome Condensation Induced by Fostriecin Does Not Require p 34$^{cdc2}$ Kinase Activity and Histone H1 Hyperphosphorylation, but Is Associated with Enhanced Histone H2A and H3 Phosphorylation. The EMBO Journal, vol. 14, No. 5, pp. 976–985 (1995).
Duncan T. Ho, et al. The Antitumor Drug Fostriecin Induces Vimentin Hyperphosophorylation and Intermediate Filament Reorganization. Carcinogenesis, vol. 17, No. 5, pp. 967–972 (1996).
Theodore J. Boritzki, et al. Inhibition of Type II Topoisomerase by Fostriecin, Biochemical Pharmacology, vol. 37, No. 21, pp. 4063–4068 (1988).
Hilary Anderson, et al. Topoisomerase II Inhibitors Affect Entry into Mitosis and Chromosome Condensation in BHK Cells, Cell Growth & Differentiation, vol. 7, pp. 83–90 (Jan. 1996).
Wojciech Gorczyca, et al. Induction of DNA Strand Breaks Associated with Aopotosis during Treatment of Leukemias, vol. 7, No. 5, pp. 659–670 (May 1993).
De–Lin Du, et al. Comparative Toxicity of Fostriecin, Hepsulfam and Pyrazine Diazohydroxide to Human and Murine Hematopoietic Progenitor Cells In Vitro, Investigatinal New Drugs, vol. 9, pp. 149–157 (1991).
Michael Roberge, et al. Antitumor Drug Fostriecin Inhibits the Mitotic Entry Checkpoint and Protein Phosphatases 1 and 2A, Cancer Research, vol. 54, pp. 6115–6121 (Dec. 1, 1994).
Armstrong et al. 1992 J Mol Cell Cardiol 24:869–884.
Deutsch et al 1990 Circulation 82:2044–2051.
Cohen et al 1995 Cardiol. Rev. 3(3):137–149.
Roberge et al. 1994 Cancer Res. 54:6115–6121.
Stryer 1991 Biochemistry 2nd Ed. WH Freenan and Company, San Francisco, pp. 818–819.

*Primary Examiner*—Karen Cochrane Carlson
*Attorney, Agent, or Firm*—Benjamin Aaron Adler

[57] ABSTRACT

Fostriecin and a compounds structurally related to fostriecin diminish myocardial infarction and delay the onset of cell injury in an ischemic heart. There is a strong correlation between myocardial protection and the inhibition of certain serine/threonine protein phosphatases. The present invention is drawn to a method for administering fostriecin as a pharmacological compound to reduce the size of a myocardial infarction. Further, administration of fostriecin is useful also as an adjunct therapy to treatment with thrombolytic agents or angioplasty to limit the size of infarction. The most advantageous feature of the method of the present invention is that administration of fostriecin diminishes infarct volume and cell injury even when added after ischemia conditions occurred. In addition to the use of the method of the present invention for limiting damage due to myocardial infarction, the method of the present invention can be employed to delay damage associated with tissue storage for organ transplantation.

13 Claims, 14 Drawing Sheets

```
                              ATG TCCGACAGCG AGAAGCTCAA
 51  CCTGGACTCG ATCATCGGGC GCCTGCTGGA AGTGCAGGGC TCGCGGCCTG
101  GCAAGAATGT ACAGCTGACA GAGAACGAGA TCCGCGGTCT GTGCCTGAAA
151  TCCCGGGAGA TTTTTCTGAG CCAGCCCATT CTTCTGGAGC TGGAGGCACC
201  CCTCAAGATC TGCGGTGACA TACACGGCCA GTACTACGAC CTTCTGCGAC
251  TATTTGAGTA TGGCGGTTTC CCTCCCGAGA GCAACTACCT CTTTCTGGGG
301  GACTATGTGG ACAGGGGCAA GCAGTCCTTG GAGACCATCT GCCTGCTGCT
351  GGCCTATAAG ATCAAGTACC CCGAGAACTT CTTCCTGCTC CGTGGGAACC
401  ACGAGTGTGC CAGCATCAAC CGCATCTATG GTTTCTACGA TGAGTGCAAG
451  AGACGCTACA ACATCAAACT GTGGAAAACC TTCACTGACT GCTTCAACTG
501  CCTGCCCATC GCGGCCATAG TGGACGAAAA GATCTTCTGC TGCCACGGAG
551  GCCTGTCCCC GGACCTGCAG TCTATGGAGC AGATTCGGCG GATCATGCGG
601  CCCACAGATG TGCCTGACCA GGGCCTGCTG TGTGACCTGC TGTGGTCTGA
651  CCCTGACAAG GACGTGCAGG GCTGGGGCGA GAACGACCGT GGCGTCTCTT
701  TTACCTTTGG AGCCGAGGTG GTGGCCAAGT TCCTCCACAA GCACGACTTG
751  GACCTCATCT GCCGAGCACA CCAGGTGGTA GAAGACGGCT ACGAGTTCTT
801  TGCCAAGCGG CAGCTGGTGA CACTTTTCTC AGCTCCCAAC TAC TGTTATC
     GTTGTGGTAA CCAAGCTGCA ATCATGGAAC TTGATGATAC TCTAAAATAC
     TCTTTCTTGC AGTTTGACCC AGCACCTCGC AGAGGCGAGC CACATGTTAC
     TCGTCGTACC CCAGACTACT CCTGTAA TGA
```

FIGURE 6

METHOD FOR DIMINISHING MYOCARDIAL INFARCTION USING PROTEIN PHOSPHATASE INHIBITORS

This application is a continuation of provisional application Ser. No. 60/027,809, filed Oct. 4, 1996, now abandoned.

FEDERAL FUNDING LEGEND

The present invention was supported in part by Federal funds, NIH Grant CA 60750. The United States Government may have rights to this invention.

BACKGROUND OF THE INVENTION

1. Field of the Invention

The present invention relates generally to a method for administering protein phosphatase inhibitors to an individual to diminish myocardial infarction and minimize cell injury or death in ischemic tissue. Specifically, the present invention relates to a method for administering fostriecin, or a compound structurally related to fostriecin, to an individual to diminish myocardial infarction and delay cell injury or death in ischemic cardiac tissue following infarction. Beneficial therapeutic effects are achieved when fostriecin, or a compound structurally related to fostriecin, is administered either before or after the onset of a myocardial infarction.

2. Description of the Related Art

In Western countries, myocardial infarction is among the most common diagnoses in hospitalized patients. In the United States, approximately 1.5 million myocardial infarctions (MIs) occur each year, and mortality with acute infarction is approximately 30 percent (Pasternak, R. and Braunwald, E., *Acute Myocardial Infarction*, HARRISON'S PRINCIPLES OF INTERNAL MEDICINE, 13th Ed., McGraw Hill Inc., p.p. 1066–77 (1994)). More than half of the deaths that result from myocardial infarction occur before the patient reaches the hospital, and an additional 5–10% of survivors die in the first year (Pasternak, R. C. and Braunwald, E. Acute Myocardial Infarction, HARRISON'S PRINCIPLES OF INTERNAL MEDICINE, 13th Ed., McGraw Hill Inc., p.p. 1066–77 (1994)).

Myocardial infarction occurs generally with an abrupt decrease in coronary blood flow that follows a thrombotic occlusion of a coronary artery. The occluded artery often has been narrowed previously by atherosclerosis, and the risk of recurrent nonfatal myocardial infarction persists in many patients. Ultimately, the extent of myocardial damage caused by the coronary occlusion depends upon the "territory" supplied by the affected vessel, the degree of occlusion of the vessel, the amount of blood supplied by collateral vessels to the affected tissue, and the demand for oxygen of the myocardium whose blood supply has suddenly been limited (Pasternak, R. and Braunwald, E. Acute Myocardial Infarction, HARRISON'S PRINCIPLES OF INTERNAL MEDICINE, 13th Ed., McGraw Hill Inc., p.p. 1066–77 (1994)).

Because acute myocardial infarction frequently results in death, scientists and physicians have been studying the effects of myocardial ischemia for many years. It is hoped that, through better understanding of the processes involved in myocardial infarction, methods to minimize the deleterious effects produced by an abrupt decrease in myocardial blood flow can be developed. However, since the onset of a myocardial infarction usually cannot be predicted, the ideal treatment regime would be one that is effective when administered after the onset of the infarction process. Developing treatments that limit damage to the myocardium after the initiation of the infarction process poses a tremendous challenge.

The prognosis in acute myocardial infarction is largely related to the extent of mechanical ("pump" failure of the heart) or electrical (arrhythmia) complications. Ventricular fibrillation is the most common cause of arrhythmic failure, with death frequently occurring before the patient can reach a hospital. However, pump failure is the primary cause of in-hospital death from acute myocardial infarction, and there is a strong correlation between the degree of pump failure, the extent of ischemic necrosis, and mortality (Pasternak, R. and Braunwald, E., Acute Myocardial Infarction, HARRISON'S PRINCIPLES OF INTERNAL MEDICINE, 13th Ed., McGraw Hill Inc., p.p. 1066–77 (1994)).

An important development in the care of patients that suffer from an acute myocardial infarction is the use of pharmacologic or mechanical techniques to induce early reperfusion of the ischemic myocardium. Such techniques can "salvage" the tissue before it becomes damaged irreversibly. Since most acute myocardial infarctions are caused by thrombotic occlusion, thrombolytic agents (e.g. tissue plasminogen activator, streptokinase, and an isolated plasminogen streptokinase activator complex) can often restore coronary artery flow. Blood flow also can be restored mechanically with primary percutaneous transluminal coronary angioplasty.

Percutaneous transluminal coronary angioplasty is effective in restoring perfusion in acute myocardial infarction without having to use thrombolysis, and may be slightly more effective than present pharmacologic therapy. Still, percutaneous transluminal coronary angioplasty is expensive, requires highly trained personnel, and is limited seriously by facility requirements and other logistic considerations.

The clinical success achieved with percutaneous transluminal coronary angioplasty and thrombolytic agents has instigated a search for other mechanisms to limit the extent of ischemic damage. Of particular value would be the development of pharmacologic agents that delay the onset of cell death under ischemic conditions, compounds that enhance the survival of tissues after an ischemic episode, and/or drugs that diminish cell injury associated with reestablishment of blood flow or reperfusion. Such agents, used alone, should limit infarction size; however, they may be even more useful when employed as an adjunct to thrombolytic or percutaneous transluminal coronary angioplasty therapy.

With the exception of percutaneous transluminal coronary angioplasty and thrombolytic therapy, there are few indications that procedures to reduce the size of ischemic damage can be developed. However, the study of Murry et al., *Circulation* 74:1124–36 (1986), demonstrated that a significant amount of the myocardium that normally infarcts following a coronary occlusion in dogs could be salvaged if the artery was subjected first to controlled, brief occlusions, and then reperfused prior to the prolonged, myocardial infarction-causing occlusion. This phenomenon, referred to as ischemic preconditioning, was subsequently reported to occur in rabbits, pigs, rats and isolated hearts (Cohen M., et al., *Cardiol. Rev.* 3(3):137–49 (1995)). Claims that preconditioning has beneficial effects in humans have also been made (Deutsch, et al., *Circulation*, 82:2044–51 (1990); and Yellon, et al., *Lancet*, 342:276–77 (1993)), resulting in investigations to determine the biochemical mechanism(s) by which preconditioning leads to protection.

A possible mechanism underlying the basis for preconditioning came from studying the events that followed the onset of ischemia. Such studies revealed that many agents are released by the myocardium during ischemia, including adenosine, catecholamines, angiotensin II, bradykinin and endothelin (Cohen, et al., *Ann. Rev. Med.* 47:21–29 (1996)). Initial studies focused on adenosine, and it was found that drugs that block cell surface adenosine receptors completely nullified protection (see Cohen, et al., *Ann. Rev. Med.* 47:21–29 (1996); and Liu, et al., *Circulation,* 84:350–56 (1991)). This suggested protection may be receptor-mediated. Further, infusion of adenosine $A_1$-selective analogues in lieu of preconditioning ischemia protected the heart (Liu, et al., *Circulation,* 84:350–56 (1991)). Therefore, $A_1$-receptors were suspected as being the trigger for the protection provided by ischemic preconditioning.

Like adenosine, endogenous release of bradykinin during ischemia, or intravenous infusion of this agent, successfully preconditions rabbit myocardium, and a $B_2$-receptor antagonist blocks this effect. Inhibitors of other protein kinase C-coupled receptors, as well as antagonists of protein kinase C itself, also abort protection from ischemic preconditioning; and protein kinase C activators can substitute for brief ischemia and salvage ischemic myocardium in some model systems ( Cohen, et al., *Cardiol. Rev.* 3(3):137–49 (1995); and Cohen, et al., *Ann. Rev. Med.* 47:21–29 (1996)). Thus, preconditioning may arise from a series of events and the coordination of action of many interconnected pathways; or, alternatively, preconditioning may be triggered by different signal transduction pathways that act in a parallel manner.

Although studies on ischemic preconditioning have produced a better understanding of the biochemical mechanisms underlying the phenomenon, to date none of the insight has led to the production of clinically useful agents for the treatment of myocardial infarction. First, all of the aforementioned compounds have the requirement of pre-treatment (treatment before the myocardial infarction episode), and there are very few situations where a physician can anticipate an impending coronary occlusion, though such a procedure may be useful where a myocardial infarction occurs to a patient during an operation. Second, it has been found that chronic treatment with an $A_1$-selective agonist produced tolerance within 3 days, because of either a down-regulation or decreased sensitivity of the adenosine receptor itself (Cohen, et al., *Cardiol. Rev.* 3(3):137–49 (1995); and Tsuchida, et. al., *J. Mol. Cell Cardiol.* 26:303–311 (1994)).

The prior art is deficient in the identification of pharmacological agents that can diminish myocardial infarction and delay cell injury or death in ischemic cardiac tissue after the onset of myocardial infarction. The present invention fulfills this long-standing need and desire in the art.

SUMMARY OF THE INVENTION

One object of the present invention is to provide a method for administering protein phosphatase inhibitors to an individual to diminish myocardial infarction and minimize cell injury or death in ischemic cardiac tissue.

In a specific embodiment of the present invention, there is provided a method for administering fostriecin, or a compound structurally related to fostriecin, to an individual to diminish myocardial infarction and delay cell injury or death in ischemic cardiac tissue.

In one embodiment of the present invention, there is provided a method for administering fostriecin, or a compound structurally related to fostriecin, to an individual to be treated before myocardial infarction occurs to said individual, so as to prevent or diminish myocardial infarction and/or delay cell injury or death in ischemic cardiac tissue.

In another embodiment of the present invention, there is provided a method for administering fostriecin, or a compound structurally related to fostriecin, to an individual to be treated after the onset of a myocardial infarction to said individual, so as to diminish the size, extent or severity of said myocardial infarction and to delay cell injury or death in ischemic cardiac tissue.

Another embodiment of the present invention includes providing a method for administering compounds that have inhibitory activity against certain serine/threonine protein phosphatases (phosphatases containing the amino acid sequence RGNHE) (SEQ ID NO. 1), either before or after the onset of a myocardial infarction, to an individual to diminish myocardial infarction and delay cell injury/death in ischemic cardiac tissue.

In a particular embodiment of the present invention, the protein phosphatase inhibitors are administered to achieve a final concentration of about 0.1 $\mu$M to about 500 $\mu$M in infarcted tissue.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 1A: Employing a well-characterized rabbit model, a controlled coronary occlusion was employed to induce myocardial infarction in isolated rabbit hearts.

In control rabbits, a 30-minute coronary occlusion produces an average infarct size that is 33% of the risk zone. When the heart was perfused with 1 $\mu$M fostriecin, a significant decrease in infarct size to 9% of the risk zone was obtained. No hemodynamic effects were observed with fostriecin. Data from individual animals are shown as open circles with the mean ± SE depicted with filled circles.

Figure 1A:
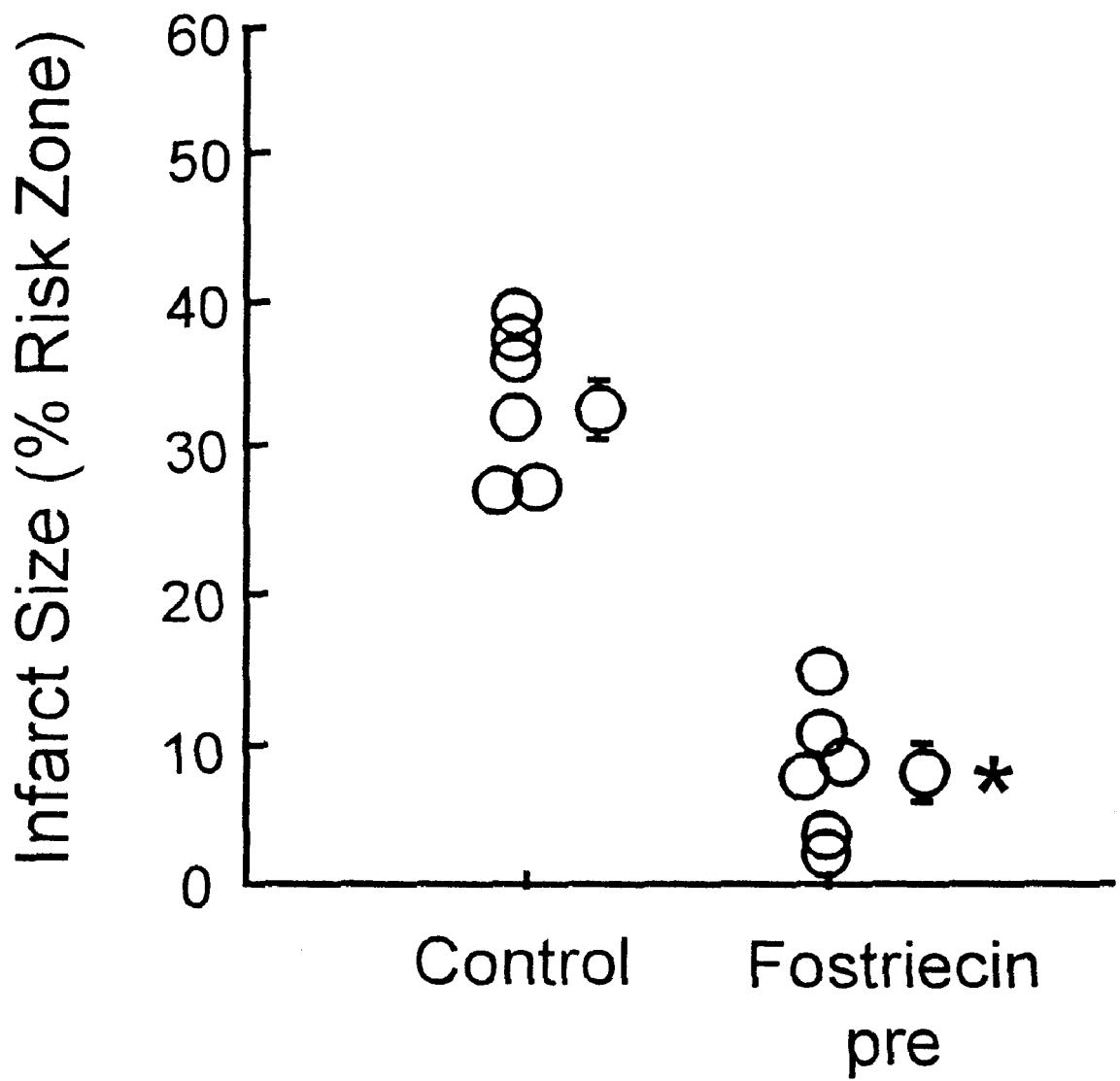
FIGS. 1A and 1B: Treatment of the heart with 1 $\mu$M fostriecin reduces infarction size in rabbit hearts.
Figure 1B:
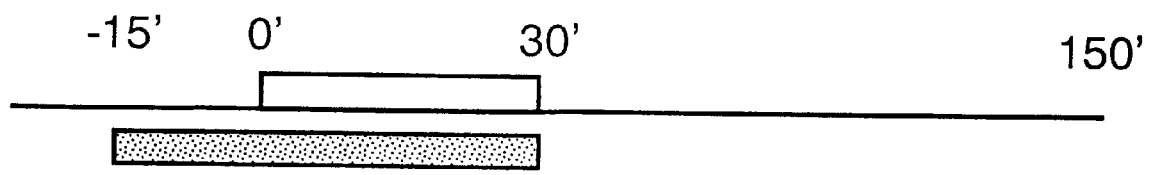

FIG. 1B: Perfusion. Fostriecin was administered 15 minutes prior to the onset of ischemia and present during the 30-minute ischemic period. The ischemic period is designated as an open rectangle; fostriecin perfusion is indicated by a filled rectangle; Time is indicated in minutes with 0 denoting the onset of the 30-minute ischemic period.

Figure 2A:
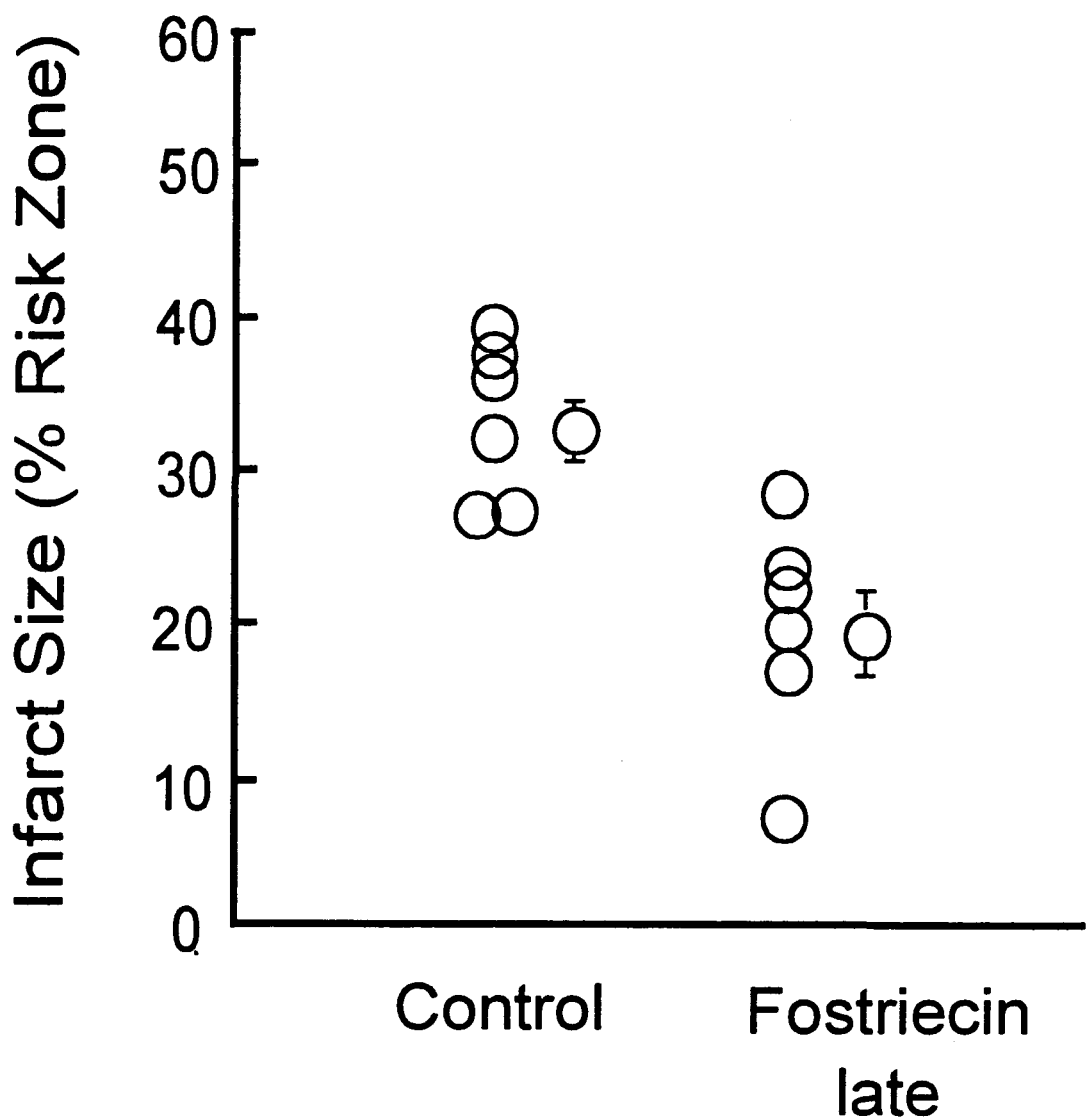
Figure 2B:
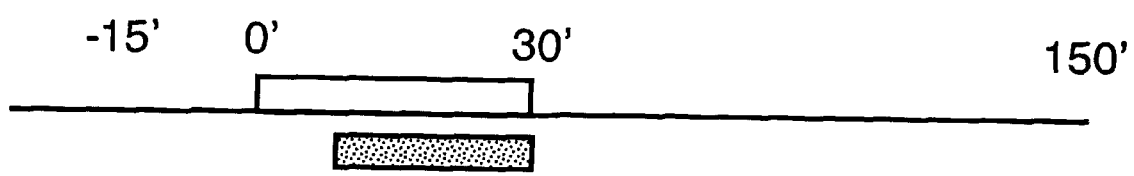

FIGS. 2A and 2B: Treatment of the heart with fostriecin 10 minutes into the ischemic period also reduces infarction size in rabbit hearts.

FIG. 2A: Employing the same experimental model described in FIG. 1, the addition of 10 $\mu$M fostriecin 10 minutes after the onset of ischemia decreased infarction size to 19% of the risk zone. While the protection observed with post-treatment was not as great as that observed with pre-treatment (FIG. 1), infarction was still 43% smaller than in untreated hearts. Data from individual animals is shown as open circles with the mean ± SE depicted with filled circles.

FIG. 2B: Perfusion. Fostriecin was administered 10 minutes after the onset of ischemia and was present during the remainder of the 30 minute ischemic period. The ischemic period is as an open rectangle; fostriecin perfusion is indicated by a filled rectangle; Time is indicated in minutes with 0 denoting the onset of the 30-min ischemic period.

Figure 3:
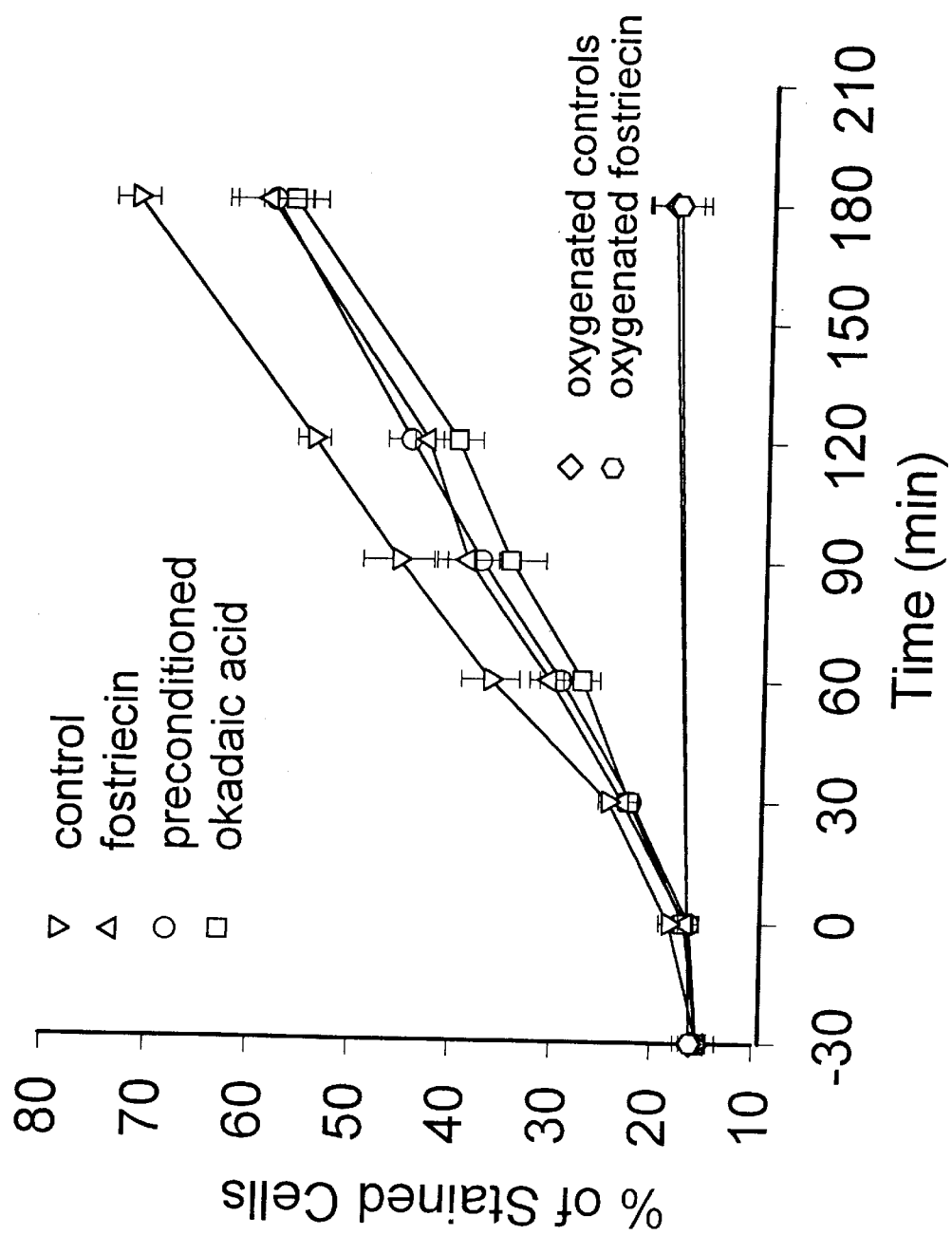

FIG. 3: Effect of fostriecin on myocyte integrity. The percentage of trypan blue-staining cells following osmotic stress was evaluated in control cells (x), and cells treated with 10 μM fostriecin added during the entire ischemic period (.). When fostriecin (10 μM) was added to the cells at the onset of ischemia, a significant reduction in cell fragility, reflected as a diminution of the area under the % time curve (10.6%•hr vs. 14.3%•hr in untreated cells), was observed.

Figure 4:
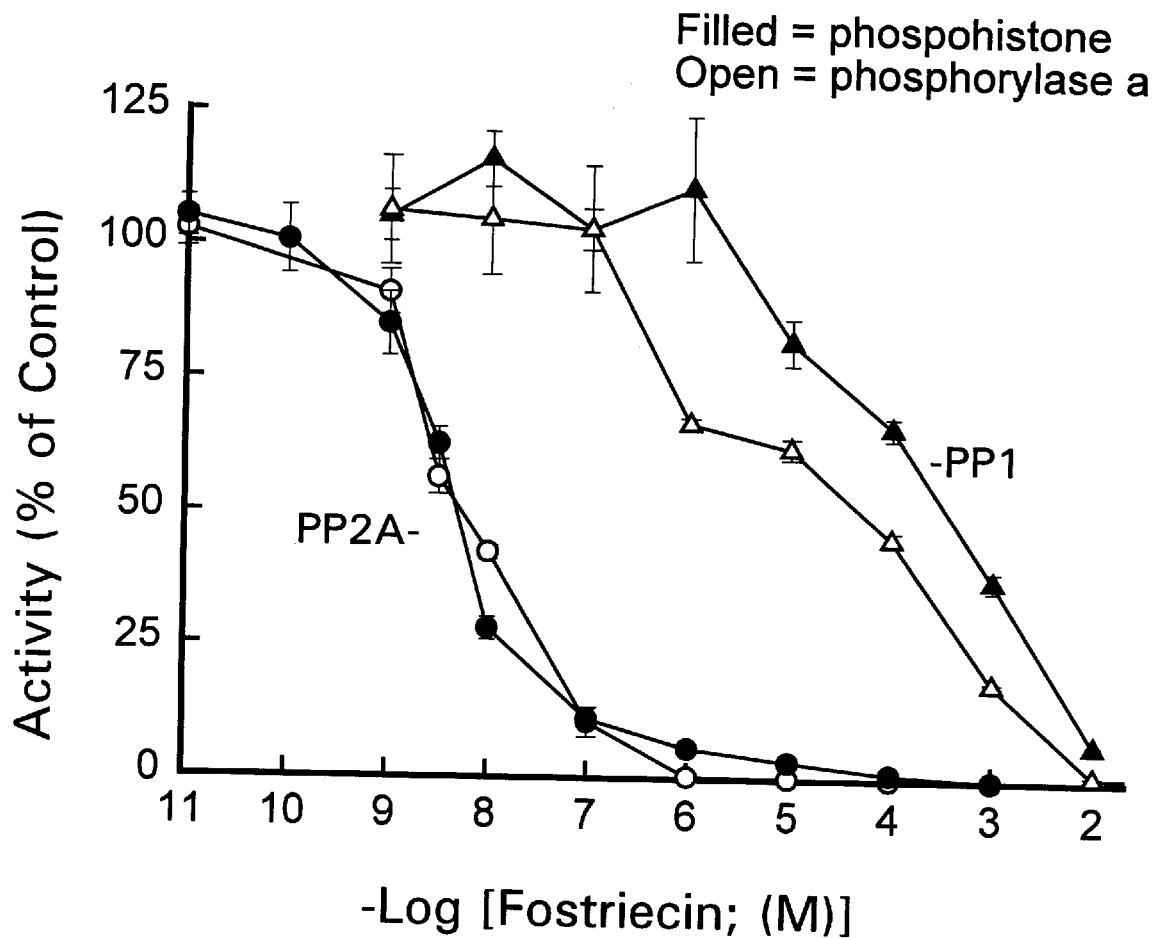

FIG. 4: Effect of fostriecin on the activity of protein phosphatase type 1 (PP1) and protein phosphatase type 2A (PP2A). The activity of the purified catalytic subunits of PP1 (Δ,s) or PP2A (O,1) was assayed in the presence of the indicated amount of fostriecin. The inhibition assays employed freshly prepared [$^{32}$P]-phosphohistone (open symbols) or [$^{32}$P]phosphorylase A (filled symbols) as substrate and highly purified catalytic subunits of PP1 or PP2A. Assays were conducted in a total volume of 80 μl, and the indicated amount of fostriecin was added to the assay 10 minutes prior to initiation of the reaction by the addition of substrate. Each point represents the mean ± SE (n>6).

Figure 5:
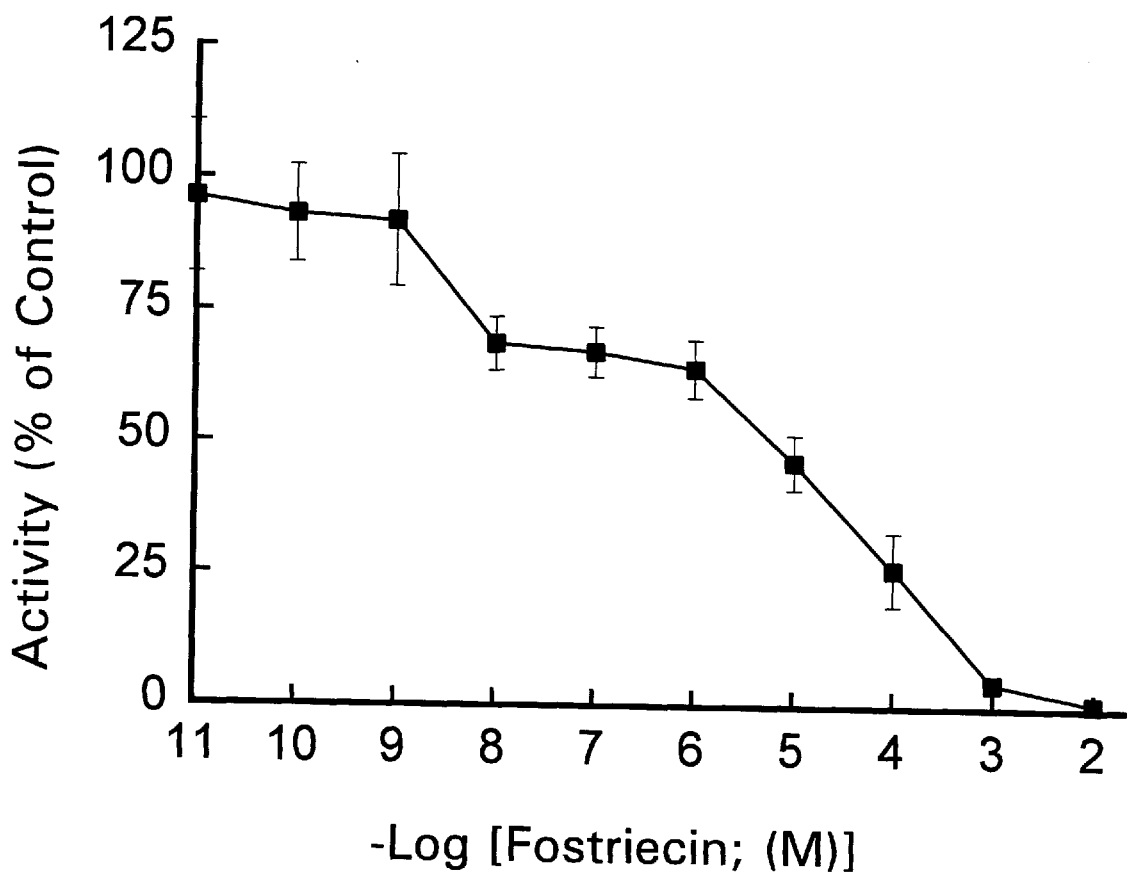

FIG. 5: Effect of fostriecin on the divalent cation-independent phosphatase activity contained in a dilute, whole cell homogenate of rabbit ventricle. Dilute homogenates of rabbit ventricle biopsies were assayed in the presence of the indicated amount of fostriecin. The inhibition assays employed [$^{32}$P]-phosphohistone as substrate, and preliminary studies indicated that protein phosphatase activity was linear with respect to protein concentration and time. Assays were conducted in a total volume of 80 μl, and the indicated amount of fostriecin was added to the assay 10 minutes prior to initiation of the reaction by the addition of substrate. Each point represents the mean ± SE (n>6).

FIG. 6: Sequence of a PP1/PP2A chimera. To characterize the fostriecin binding site, the N-terminal region of PP1 was ligated to the C-terminal region of PP2A (in bold) to produce a PP1/PP2A-chimera (CRHM2). Previous studies indicate that the okadaic acid binding domain is contained in the C-terminal region of PP2A that was incorporated into CRHM2.

Figure 7A:
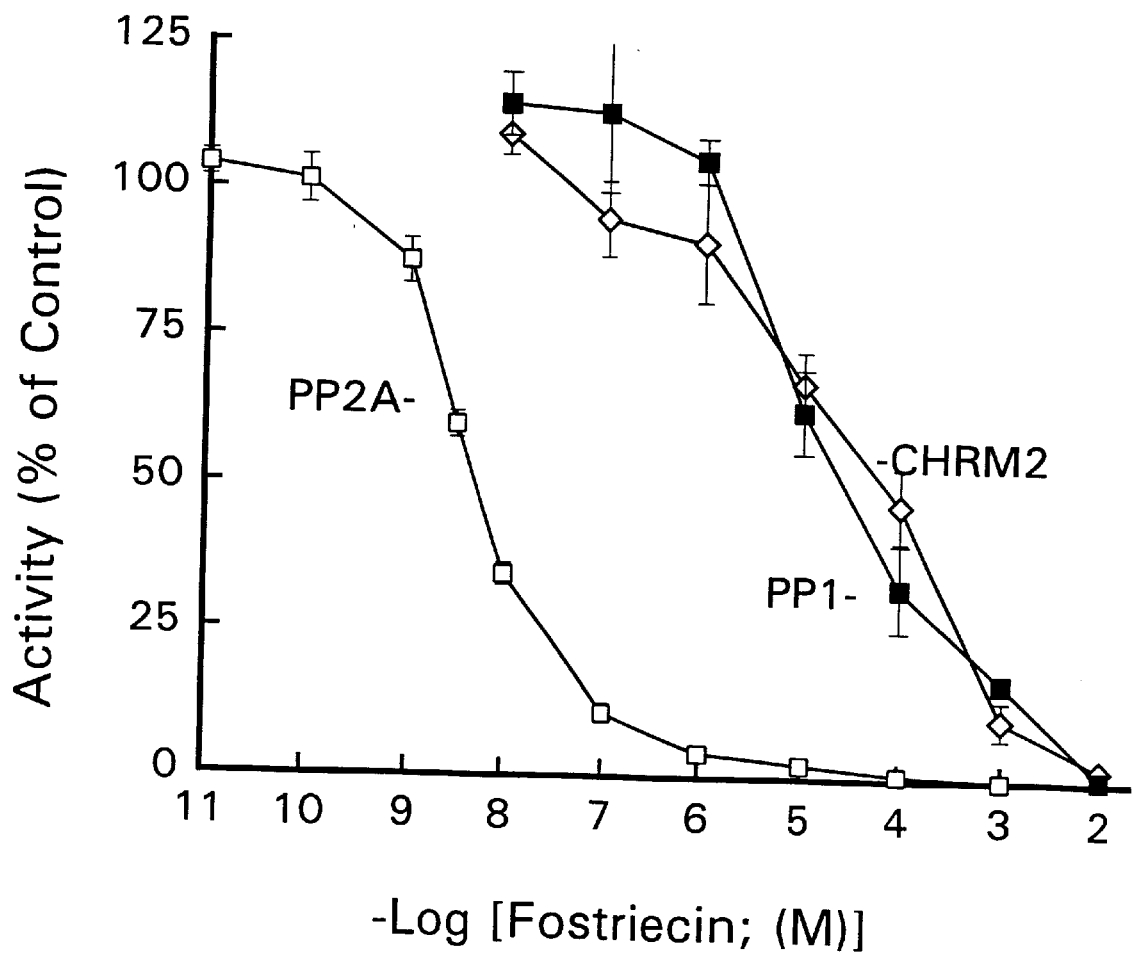
Figure 7B:
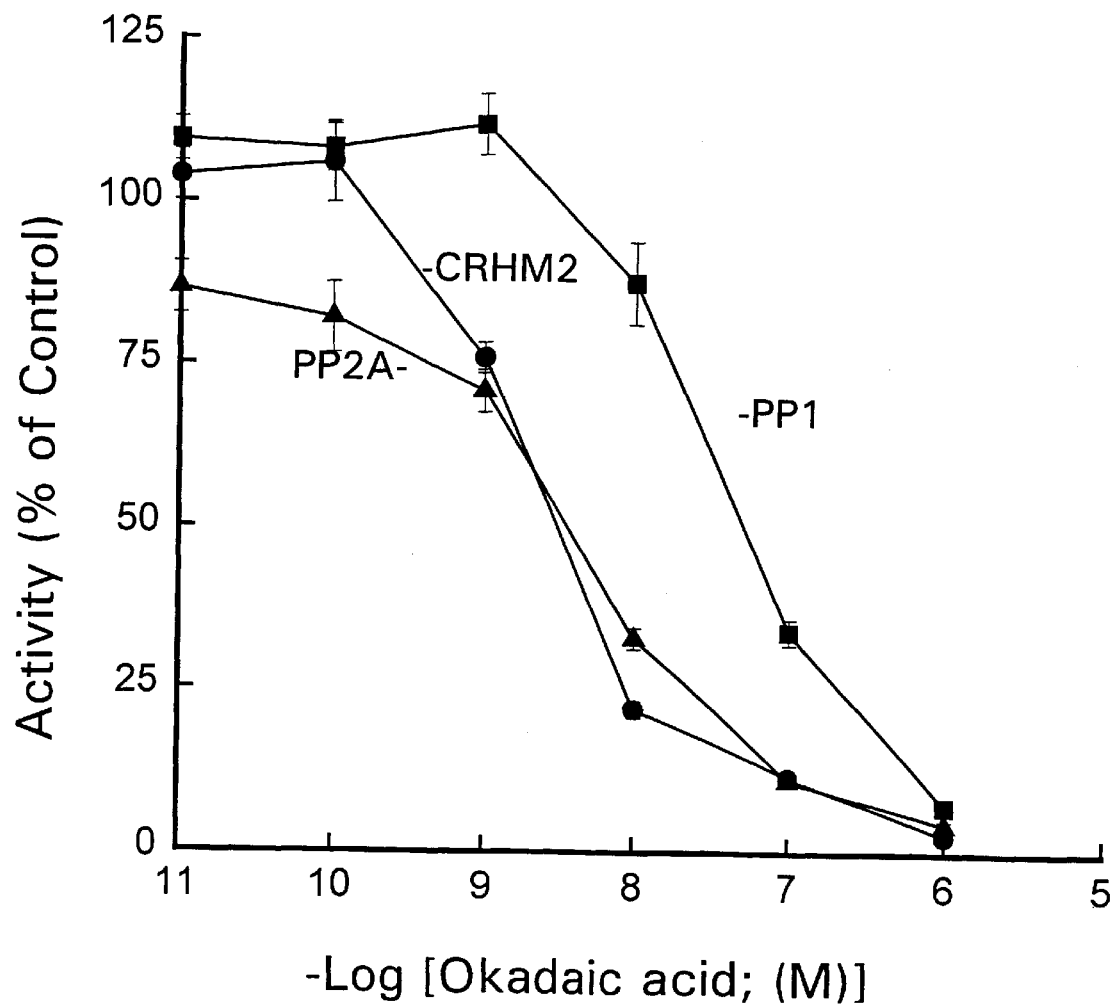

FIG. 7: Effect of fostriecin and okadaic acid on the activity of recombinant CRHM2. CRHM2 activity was assayed in the presence of the indicated amount of fostriecin (FIG. 7A) or okadaic acid (FIG. 7B). The inhibition assays employed [$^{32}$P]-phosphohistone as substrate, and preliminary studies indicated that protein phosphatase activity was linear with respect to protein concentration and time. Assays were conducted as described in FIG. 5. Each point represents the mean ± SE (n>6).

Figure 8A:
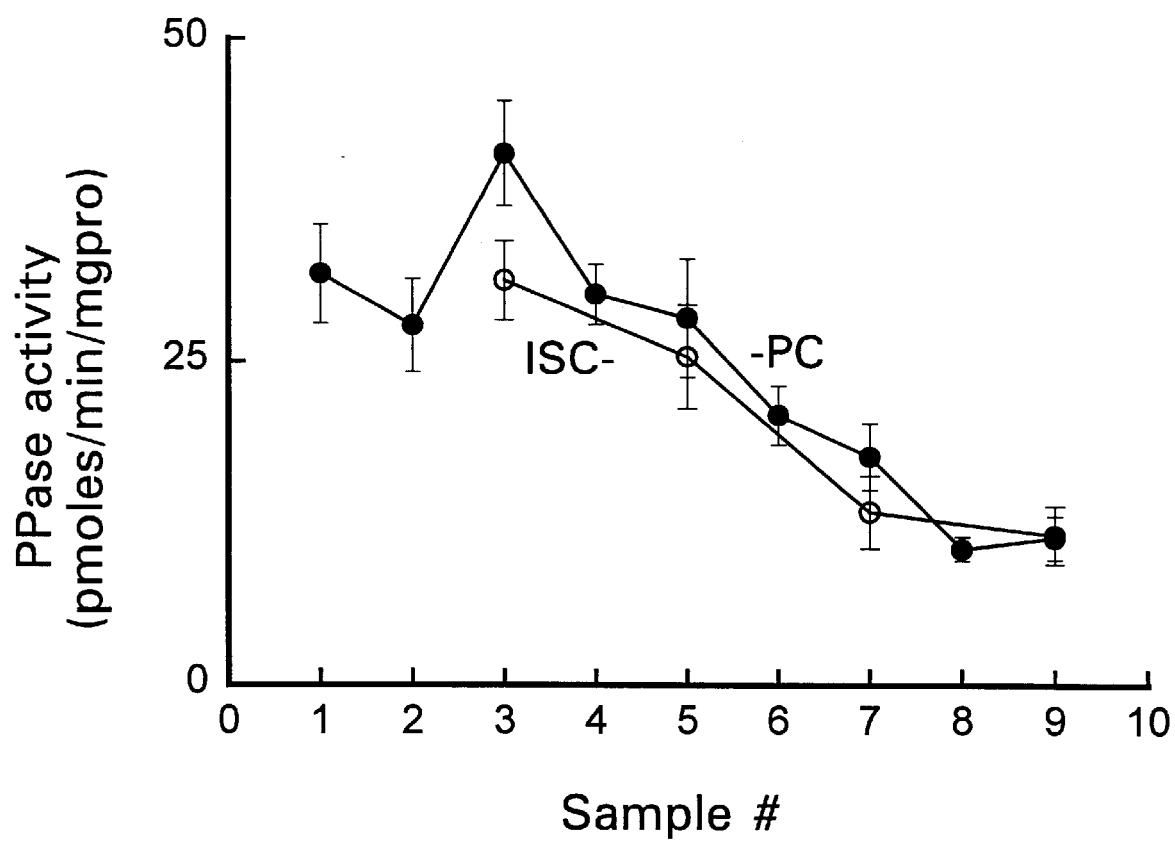

FIG. 8A: Effect of ischemic preconditioning on the okadaic acid-resistant divalent cation-independent phosphatase activity (PP1/PP4/PP5) contained in a dilute whole cell homogenate of rabbit ventricle biopsies taken during a 30-minute period of ischemia. Isolated rabbit hearts were subjected to 30 minutes of continuous ischemia with (PC) or without (ISC) being first preconditioned by a 5-min period of ischemia. Dilute homogenates of each biopsy were assayed in the presence of 2 nM okadaic acid employing [$^{32}$P]-phosphohistone as substrate. Assays were conducted as described in FIG. 5. Each point represents the mean ±SE of 6–10 assays produced from biopsies from at least 4 different rabbits.

Figure 8B:
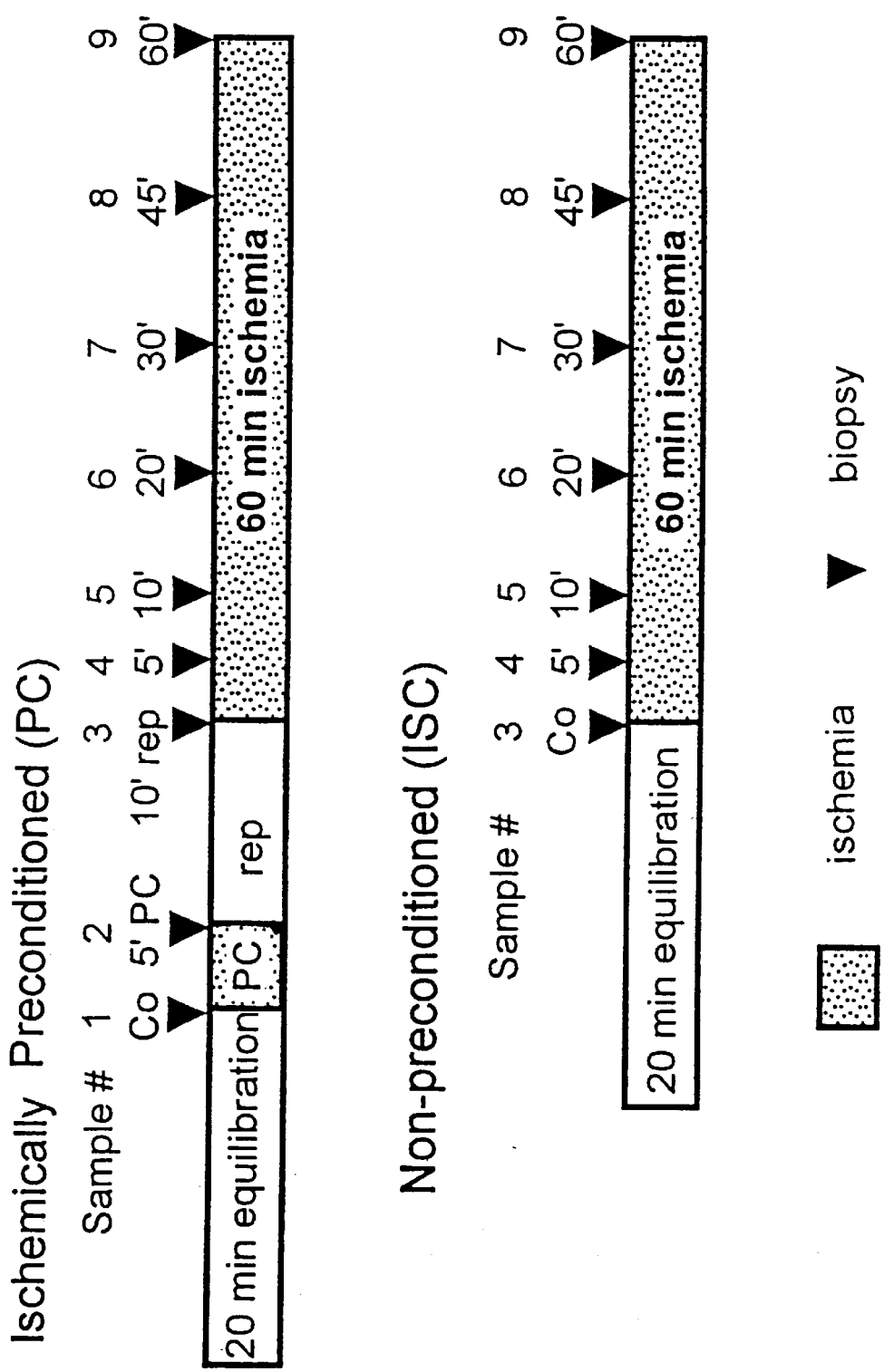

FIG. 8B: Perfusion. PC; preconditioning (5 min); REP, reperfusion (10 min); (t) indicates time when biopsies were taken.

Figure 9:
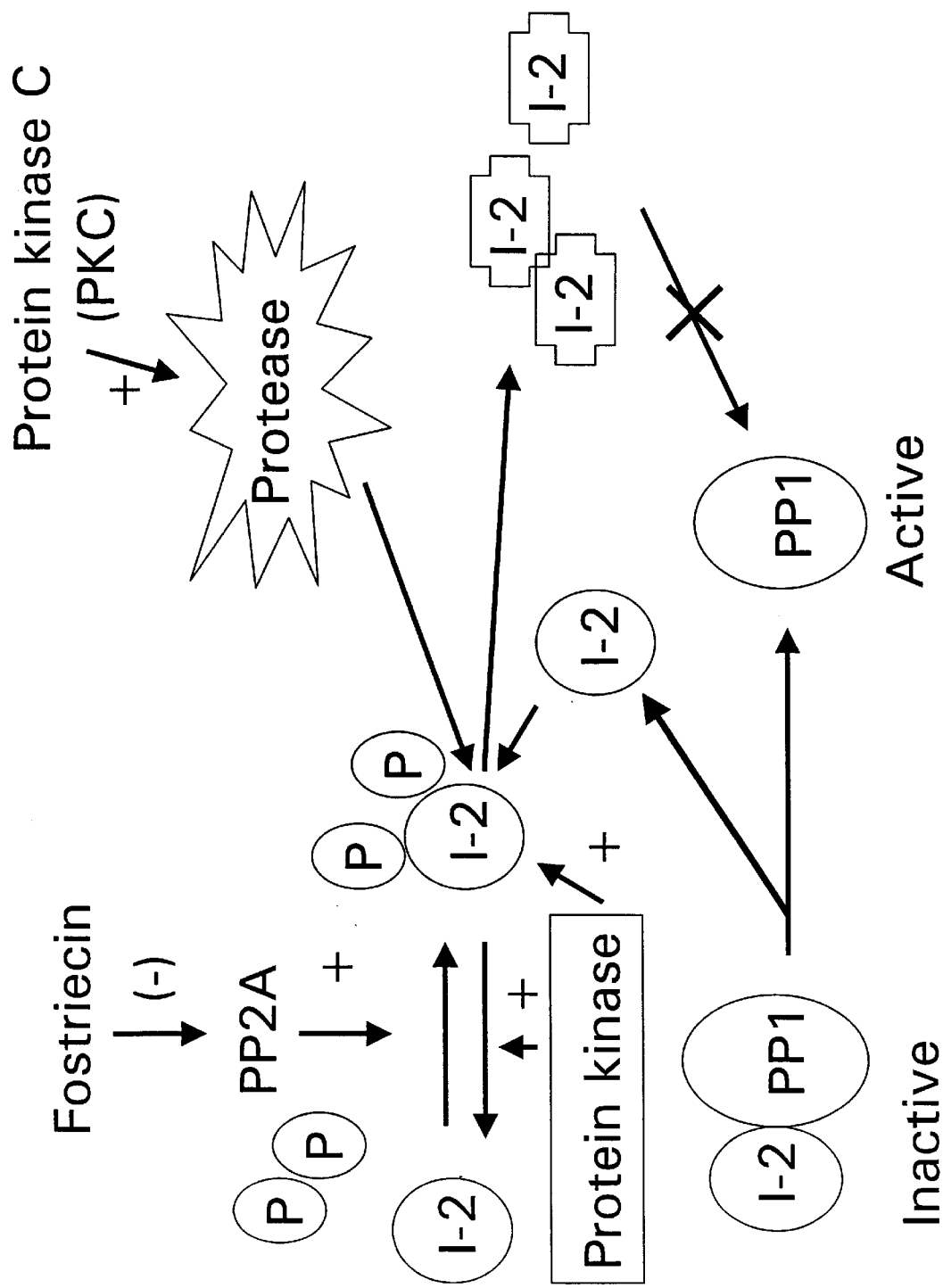

FIG. 9: Model that explains the observed data.

Figure 10:
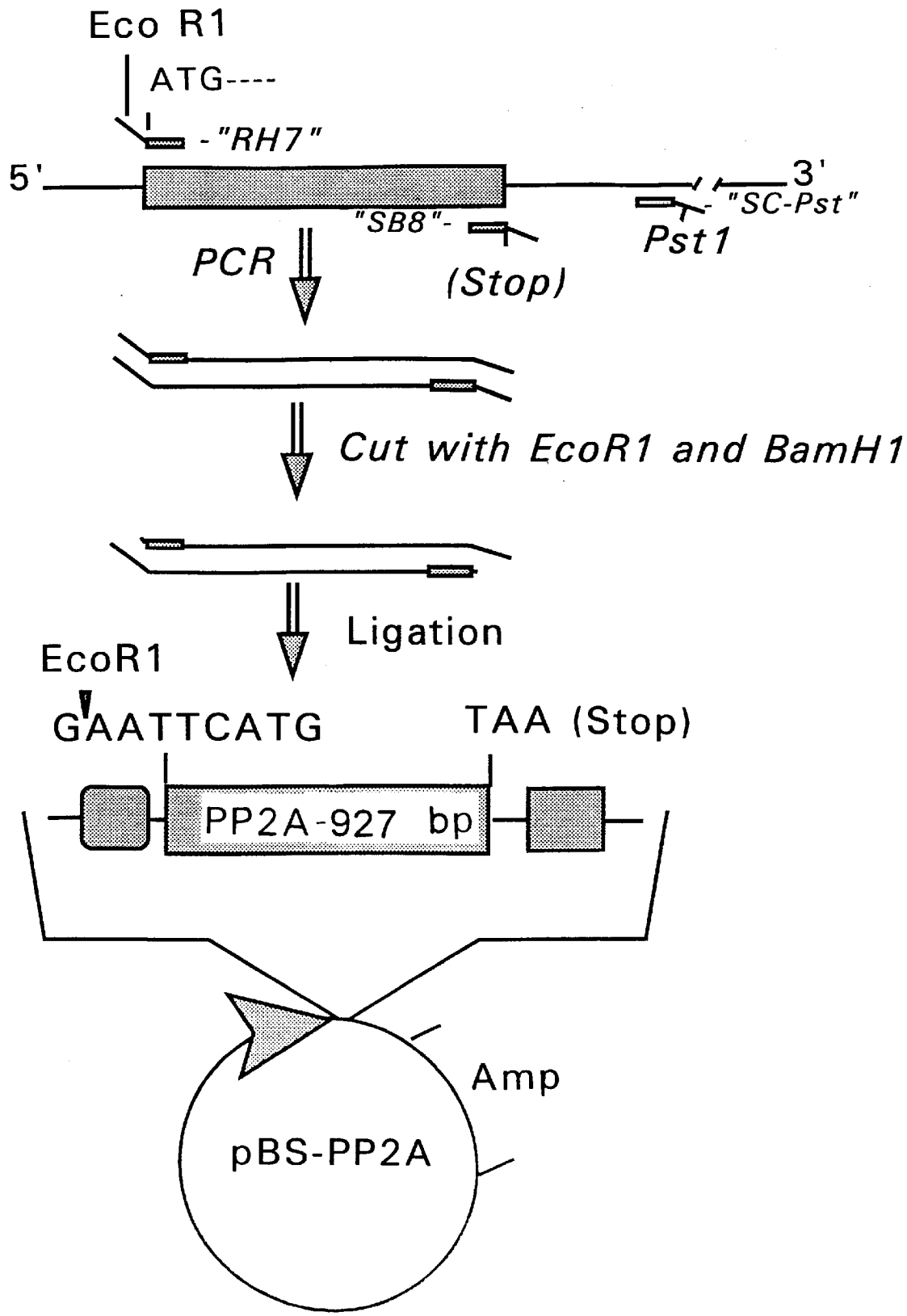

FIG. 10: PCR-based cloning strategy used to obtain the clone of PP2A, PP1 and rPP2Ac-1. The construction of pBS-PP2A is illustrated; however, the same strategy was used to produce PP1 and rPP2Ac-1.

DETAILED DESCRIPTION OF THE INVENTION

As used herein, the term "infarction" refers to necrotic changes resulting from obstruction of an end artery. A "myocardial infarction" refers to necrotic changes in the myocardium or heart muscle that results from obstruction of an end artery.

As used herein, the term "ischemia" refers to a local anemia due to obstruction of the blood supply. "Cardiac ischemia" refers to a decrease in the blood supply to the heart or cardiac tissue caused by constriction or obstruction of the blood supply.

As used herein, the term "protein phosphatase" refers to the group of enzymes that liberates inorganic phosphate from phosphoryl serine, threonine, and/or tyrosine residues of a protein. Since the catalytic properties of many enzymes are markedly altered by the covalent attachment of phosphoryl groups (i.e. the phosphorylation of serine, threonine or tyrosine residues), dephosphorylation can often alter the biological activity of a protein. Serine/threonine protein phosphatases are a subfamily of protein phosphatases that dephosphorylate preferentially phosphoryl-serine and/or -threonine residues from a protein. Tyrosine protein phosphatases are a subfamily of protein phosphatases that preferentially dephosphorylate tyrosine residues from a protein.

As used herein, the term "protein kinase" refers to an enzyme that catalyzes the phosphorylation of serine, threonine or tyrosine residues of a protein by facilitating the transfer of the terminal phosphate from ATP (and/or possibly GTP) to the side chain of serine, threonine, or tyrosine. Phosphorylation often alters the biologic activity of a protein.

As used herein, the term "fostriecin" refers to a unique pharmacological agent first isolated from the fermentation broth of a subspecies of *Streptomyces pulveraceus* (subspecies fostreus: ATCC 31906) that inhibits the activity of certain protein phosphatases and diminishes the size of a myocardial infarction. The structure of fostriecin is as follows:

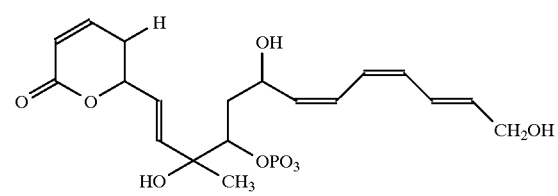

As used herein, the term "compound structurally related to fostriecin" refers to compounds derived by the synthetic modification of fostriecin and which retain fostriecin-like enzymatic activity, inhibiting protein phosphatases. The "compounds structurally related to fostriecin" have a base structure of:

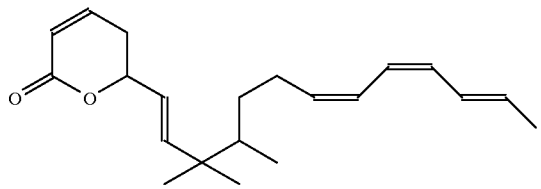

As used herein, the term "ischemic pre-conditioning" or "pre-conditioning" refers to the process whereby an artery is occluded and reperfused for brief periods prior to the prolonged occlusion of the artery resulting in infarction. In the process of ischemic pre-conditioning, a significant amount of the myocardium that normally infarcts following the coronary occlusion is not damaged.

As used herein, the term "risk zone" shall mean the tissue normally supplied with oxygenated blood by the coronary artery before the artery is occluded.

As used herein, the term "therapeutically effective amount" of an agent shall refer to an amount of that agent which is physiologically significant and improves an individual's health. An agent is "physiologically significant" if its presence results in a change in the physiology of the recipient human. For example, in the treatment of a pathological condition, administration of an agent which relieves or arrests further progress of the condition would be considered both physiologically significant and therapeutically effective.

The present invention is directed to methods for administering fostriecin, or a compound structurally related to fostriecin, to an individual to diminish myocardial infarction and delay cell injury or death in ischemic cardiac tissue. It is contemplated that beneficial therapeutic effects will be achieved if fostriecin, or a compound structurally related to fostriecin, is administered either before or after the onset of a myocardial infarction. For therapeutic applications, a person having ordinary skill in the art of molecular pharmacology would be able to determine, without undue experimentation, the appropriate dosages and routes of administration of the novel pharmacological compounds of the present invention.

The following examples are given for the purpose of illustrating various embodiments of the invention and are not meant to limit the present invention in any fashion:

EXAMPLE 1

Controlled Coronary Occlusion, Drug Perfusion, and Measurement of Infarct Size and Ischemic Risk Zone New Zealand white rabbits were anesthetized with intravenous sodium pentobarbital (30 mg/kg). The trachea was intubated and mechanical ventilation was achieved. After a left thoracotomy, a snare was passed around the coronary artery and the hearts were excised quickly, mounted on a Langendorff apparatus and perfused at 75 mm Hg pressure with non-recirculating Krebs buffer containing 118.5 mM NaCl, 4.7 mM KCl, 1.2 mM $MgSO_4$, 1.2 mM $KH_2PO_4$, 24.8 mM $NaHCO_3$, 2.5 mM $CaCl_2$, and 10 mM glucose. The Krebs buffer was gassed with 95% $O_2$/5% $CO_2$ resulting in a pH of 7.4–7.5. The temperature of the perfusate was maintained at 37° C.

A fluid-filled latex balloon connected to a transducer with PE240 tubing was inserted into the left ventricle. The balloon volume was adjusted to set the left ventricular diastolic pressure equal to 5–10 mm Hg at the beginning of the experiment. Total coronary artery flow was measured by timed collection of perfusate dripping from the heart with a graduated cylinder.

The coronary artery was occluded for 30 minutes and reperfused for 2 hours. Fostriecin was mixed with oxygenated perfusate in a separate reservoir to a concentration of 1 $\mu$M. Treatment was begun by opening the line from the drug-laden reservoir and closing the line from the reservoir containing pure buffer. After 2 hours of reperfusion, the coronary artery was re-occluded, and 1–10 $\mu$m zinc cadmium sulfide fluorescent particles (Duke Scientific, Palo Alto, Calif.) were infused into the perfusate to demarcate the risk zone. The heart was removed, weighed, frozen, and cut into 2 mm thick slices. The slices were thawed and stained by incubation for 20 minutes at 37° C. in 1% triphenyltetrazolium chloride (TTC) in pH 7.4 buffer. The areas of infarct (TTC negative) and risk zone (non-fluorescent under ultraviolet light) were determined by planimetry. Infarct and risk zone volumes were calculated by multiplying each area by the slice thickness and summing the products. Infarct size for each heart was expressed as a percentage of the risk zone infarcted. In an untreated rabbit heart approximately 33% of the ischemic tissue infarcts in this model.

Isolated Myocytes: Rabbit hearts were mounted on a perfusion apparatus as described above and perfused with "high potassium/low calcium" perfusion buffer containing 125 mM NaCl, 30 mM KCl, 25 mM $NaHCO_3$, 1.2 mM $KH_2PO_4$, 1 mg/ml BSA, 1.2 mM $MgCl_2$, 11 mM glucose, 0.68 mM 1-glutamine, and a complete amino acid solution (pH 7.4) for 5 minutes. Collagenase (Worthington Biochemical, Freehold, N.J.) was added at a concentration of 1.25 mg/ml and the heart was perfused for 45–60 minutes until it became soft. The heart was removed from the apparatus and minced in 5 mls of perfusion buffer containing 0.1% w/v BSA. After gentle dispersion and filtering through a nylon mesh, the cells were washed in "low potassium" (5 mM KCl) buffer. The cells were collected and centrifuged several times to increase the proportion of viable rod-shaped cells. Calcium was added to the cells in step-wise fashion to a final concentration of 1.25 mM. The cells were suspended in 10 mls of the final wash buffer to yield approximately $12\times10^6$ cells. Cell counts and viability were assessed by removing 10 $\mu$l aliquots, mixing with an equal volume of Tyrode's solution containing 1% trypan blue, and counting within 3–5 minutes by light microscopy. At least 70% rod shaped viable cells must have been present to constitute a successful isolation.

To simulate ischemia, the suspension was divided into 4–6 conical Eppendorf tubes and each tube was spun lightly to form a 0.2–0.5 ml pellet of packed cells. The supernatant was removed and a mineral oil layer 1–2 cm thick was added to exclude air from the pellet. The tube was incubated at 37° C. without agitation for 60–120 minutes. Periodically during this "ischemic" period, an aliquot of cells was removed and suspended in hypotonic (85 mOsm) incubation medium containing 3 mM amytal to prevent reoxygenation-induced cell rounding. After incubation for 3 minutes, an aliquot of cells was mixed on a glass slide with an equal volume of 1% glutaraldehyde in modified Tyrode's solution to which 1.0% trypan blue had been added. Within 5 minutes, at least 300 cells were examined with an inverted stage microscope from multiple areas of the slide, and the numbers of rounded and rod-shaped cells and those stained with trypan blue recorded. Trypan blue permeability is used as a marker for injury because this method allows correlation of cell death with morphological changes in the cells.

The percentage of stained (dead) cells was determined, and a plot of % dead cells vs. time was constructed. An index of non-survival was calculated as the area under the curve after 2 hours and presented as %-hr. This assay does not measure cell death strictly as the endpoint, but measures the appearance of membrane fragility which occurs during ischemia and can be delayed significantly by preconditioning.

Preconditioning was accomplished by incubating the cells in glucose-free medium for 10 minutes, after which glucose was restored for 30 minutes before simulated ischemia. Preconditioning of the isolated myocytes, therefore, was done with a metabolic stimulus rather than ischemia. Examination of the effects of fostriecin was performed by adding the agent to the medium in which the cells were suspended.

EXAMPLE 2

Measurement of Protein Phosphatase Activity and the Preparations of Phosphoprotein Substrates Phosphorylase kinase (EC 2.7.1.38), protein kinase A (3':5'-cyclic AMP dependent) phosphorylase b (EC 2.4.1.1), and crude histone (type 2AS) were obtained from Sigma Chemical Co. Okadaic acid was a gift from Dr. R. Dickey (U.S. Food and Drug Administration, Dauphin Island, Ala.). Okadaic acid now can be obtained from a variety of commercial sources. Phosphohistone with a specific activity >$4.5 \times 10^6$ dpm/nmol incorporated phosphate was prepared by the phosphorylation of bovine brain histone (type 2AS from Sigma Chem. Co) with 3':5'-cAMP-dependent protein kinase (from rabbit muscle) in the presence of [$\gamma$-$^{32}$P]ATP essentially described by Honkanen et al. in Honkanen et al., J. Biol. Chem. 265:19401–04 (1990) and Honkanen et al., Mol. Pharmacol. 40:577–83 (1991). The reaction was started by the addition of protein kinase A (1 mg) to a 20 mM Tris-buffer (pH 6.2) containing 20 mg of histone, 1 mCi [$\gamma$-$^{32}$P]ATP (150 $\mu$M ATP), 100 $\mu$M cAMP, 5 mM DTT, and 5 mM MgCl$_2$. The final volume was 4 ml and the phosphorylation reaction was allowed to continue for 3.5 hours at 30° C. The reaction was terminated by the addition of 1.3 ml of ice cold 100% trichloroacetic acid, and after placing the tube in ice for 10 minutes, the precipitated phosphohistone was collected by centrifugation at 3000xg for 5 minutes. The supernatant was discarded and the pellet was redissolved in 4 ml of 0.8 M Tris-Cl (pH 8.5). Trichloroacetic acid (1.3 ml of 100% w/v) was added to precipitate the phosphohistone a second time, and the precipitation-resuspension washing procedure was repeated 5 times. The pellet produced after the final trichloroacetic acid precipitation was washed 2 times with 4 ml of ethanol:ethyl ether (1:4; v:v) and then 2 additional times with 4 ml acidified ethanol:ethyl ether (1:4; 0.1 N HCl). The washed phoshohistone pellet was allowed to air dry and resuspended in 5 mM Tris-Cl (pH 7.4).

Phosphorylase $\alpha$ was prepared essentially according to the methods described in Honkanen et al.; Mol. Pharmacol. 40:577–83 (1991). Briefly, [$^{32}$P]phosphorylase $\alpha$ was prepared by the phosphorylation of phosphorylase $\beta$ with phosphorylase kinase using 30 mg of phosphorylase b, 1.4 mCi of [$\gamma$-$^{32}$P]ATP (to give $1 \times 10^4$ cpm pmole-1) and 100 U of phosphorylase kinase. The phosphorylation reaction was carried out for 1.5 hour at pH 8.2 and 30° C. After termination of the reaction, phosphorylase a was crystallized by adjustment of the pH to 6.8 and placing the mixture on ice. The crystals were collected by centrifugation and washed extensively with 20 mM Tris-HCl, 50 mM 2-mercaptoethanol, pH 6.8. After washing, the crystals were dissolved by the addition of NaCl to achieve a final concentration of 100 mM. The solution was dialyzed overnight at 4° C. against 20 mM Tris-HCl, 50 mM 2-mercaptoethanol, pH 6.8. (2x4L). The phosphorylase a, which recrystalizes during dialysis, was redissolved in assay buffer containing 100 mM NaCl for immediate use or 100% glycerol for short term storage. This results in phosphorylase a with a specific activity of approximately $6 \times 10^6$ cpm/nmol of incorporated phosphate.

Determination of protein phosphatase activity: Protein phosphatase activity against phosphohistone was determined by the quantification of liberated [$^{32}$P] from phosphohistone according to previously established methods (see Honkanen et al., J. Biol. Chem. 265:19401–04 (1990); Honkanen et al., Mol. Pharmacol. 40:577–83 (1991); and Critz and Honkanen, Neuroprotocols 6:78–83 (1995)). Assays (80 $\mu$l final volume) were conducted in 50 mM Tris-buffer (pH 7.4) containing 0.5 mM DTT, 4 mM EDTA, and phosphoprotein (2 $\mu$M PO$_4$). The assay was initiated by the addition of substrate (30 $\mu$l) to a 1.5 ml microfuge tube containing 50 $\mu$l of dilute homogenate. Assays were conducted at 30° C. for 10 minutes and were stopped by the addition of 100 $\mu$l of 1N H$_2$SO$_4$ containing 1 mM K$_2$HPO$_4$. [$^{32}$P]Phosphate liberated by the enzyme was then extracted as a phosphomolybdate complex and measured according to the methods of Killilea et al., Arch. Biochem. Biophys. 191:638–46 (1978)). Briefly, free phosphate was extracted by adding 20 $\mu$l of ammonium molybdate (7.5% w/v in 1.4 N H$_2$SO$_4$) and 250 $\mu$l of isobutanol:benzine (1:1, v/v) to each tube. The tubes were mixed vigorously for approximately 10 seconds followed by centrifugation at 14,000xg for 2 minutes. Aliquots of the upper phase (100 $\mu$l) were removed for counting, and radioactivity was quantified with a scintillation counter.

For inhibition studies, the indicated amount of fostriecin or okadaic acid was added to the enzyme mixture 10 minutes before the reaction was initiated with the addition of substrate. Controls received solvent alone, and in all experiments the amount of enzyme was diluted to ensure that the samples were below the titration endpoint. The titration endpoint is defined as the concentration of enzyme after which further dilution no longer affects the IC$_{50}$ of the toxin, and represents a point where the concentration of enzyme used in the assay no longer approaches that of the toxin. This ensures that IC$_{50}$ represents the potency of the inhibitor alone and is not representative of a combination of potency of the toxin and titration artifacts of the assay system. Preliminary assays were also performed to ensure the dephosphorylation reaction was linear with respect to enzyme concentration and time.

EXAMPLE 3

Preparation of Purified Catalytic Subunits of Serine/Threonine Protein Phosphatases Type 1 (PP1) and 2A (PP2A)

The catalytic subunit of PP1 was purified to apparent homogeneity, demonstrating a single band upon SDS-PAGE and silver staining, using the established methods as described previously (see methods were those initially described by Brautigan et al., J. Biol. Chem. 260:4295–02). The catalytic subunit of PP2A was purified to apparent homogeneity according to established methods as described by Pallas et al., Cell 60:167–176 (1990) using G-75 Sephadex in the place of Ultrogel-AcA44 as previously reported in Brautigan et al., J. Biol. Chem. 260:4295–02 and Honkanen et al., Mol. Pharmacol 40:577–83 (1991). PP1 and PP2A both are now also available from several commercial sources.

EXAMPLE 4

Cloning and DNA Sequencing

PP2A and PP1-α were cloned from bovine brain and human retina, respectively, then engineered for use in a bacterial expression system. The PP2A clone is of the alpha subtype and consists of 1771 nucleotides (EMBL Accession number X72858). This clone contains a 163 bp 5'-untranslated region, a 927 bp coding region, and a 683 bp 3'-untranslated region. To produce recombinant PPase, PP2A was subcloned into a working vector, pBS (blue script) and then into a eukaryotic expression vector. Correct orientation of the construct was determined by comparison of PCR product migration patterns using internal- and plasmid-based primers. The coding region of pBS-PP2A was engineered for placement into selected prokaryotic expression vectors. To place the PP2A-coding region under the control of a prokaryotic plasmid directed promoter, the 5'-untranslated region had to be removed. This was accomplished by utilizing a PCR based strategy (FIG. 10).

For the PCR reaction, a 5'-(sense) primer (called RH7) was synthesized. This oligo contained the initial 15 nucleotides of the 5'-coding region, with an EcoR1 site at the 5' end. The antisense primer contained 14 bases complementary to the sense region of the 3'-coding region immediately preceding and including the stop codon (called SB8). It also contained an added BamH1 site. An antisense primer complementary to a region 34 nucleotides downstream of the stop codon with a Pst1 site was also constructed (SC-Pst1).

Using pBS-PP2A as a template and RH7 and SB8 or RH7 and SC-Pst1 as primers, respectively, the desired PCR products of approximately 930 and 960 bases were obtained. The PCR products were purified by agarose gel electrophoresis, cut from the gel, cleaned and digested with the appropriate restriction enzymes using routine procedures. The PCR products were ligated into pBS (blue script) and used to transform E. coli (DH5α). Colonies containing inserts were identified, and plasmids from selected clones were subjected to restriction analysis to confirm the presence of appropriate inserts. Two clones were selected and their inserts were sequenced to confirm the fidelity of the PCR-generated PP2A-construct. It was confirmed that the desired clone had been produced by direct sequencing (i.e. the insert contained the entire coding region of PP2A with the flanking restriction sites; now called pBS-PP2Ac).

PP1, an enzyme highly homologous to PP2A, could be expressed in a stable manner and in relatively large amounts. Thus, human PP1 was cloned and subcloned into a bacterial expression vector as was done for PP2A. PP1 was able to be expressed in a stable fashion, and rPP1 was less sensitive to inhibition by okadaic acid than PP2A. To create a hybrid enzyme (a PP1/PP2A chimera) that could be expressed stably like rPP1 but would bind okadaic acid with high affinity like PP2A, a number of mutant forms of PP1 and PP2A were constructed. Then, through mutational analysis, the okadaic acid binding domain of PP2A was identified. The okadaic acid binding domain from PP2A was cloned behind the amino terminal domain of PP1. The hybrid, referred to as CRHM-2, was subcloned into an expression vector. Restriction analysis of CRHM-2 confirmed the identity of the construct.

The recombinant enzyme can be expressed at levels comparable to that observed with PP1, the expression vector is stable, and rPP2Ac-1 binds okadaic acid with a comparable affinity to PP2A, yet it binds fostriecin with affinity comparable to that of PP1. Through a comparison of the sequence homologies between PP1 and PP2A and analysis of the inhibition data from studies with okadaic acid and fostriecin, it was concluded that the fostriecin-sensitive PPases contained several conserved sequences. The sequence RGNHE (SEQ ID NO. 1) was contained in all the fostriecin sensitive enzymes. For a general description of the molecular biological techniques employed, please see Sambrook, et al. MOLECULAR CLONING, Cold Spring Harbor Laboratory Press (1989).

EXAMPLE 5

Treatment with Fostriecin Pre-infarction Decreases the Extent of Infarct Damage Employing the well-characterized rabbit model described herein in Example 1, a controlled coronary occlusion was employed to induce reproducibly myocardial infarctions in isolated hearts. Defining the risk zone as the tissue normally supplied with oxygenated blood by the coronary artery before it is occluded, a 30 minute coronary occlusion produces an infarction that averages 33% of the risk zone (see data for control rabbits; FIG. 1). When the isolated hearts were treated with 1 μM fostriecin administered 15 minutes prior to the onset of ischemia and present during the 30 minute ischemic period, a significant decrease in infarct size to 9% of the risk zone was obtained (FIG. 1). This level of protection is equivalent to that seen in ischemic preconditioning (see Cohen M. V., et al., Cardiol. Rev. 3(3):137–49 (1995)), and represents a substantial decrease in the amount of myocardial tissue damaged. No hemodynamic effects were observed with fostriecin.

EXAMPLE 6

Treatment with Fostriecin, Post-Occlusion, Decreases the Extent of Infarct Damage Since the onset of a myocardial infarction usually cannot be predicted, a compound that provides protection when administered after the onset of ischemia is clinically far more useful than a compound that is effective only if administered before the coronary occlusion. As seen in FIG. 2, fostriecin provides myocardial protection even when added after the onset of ischemia. The addition of 10 μM fostriecin 10 minutes after the onset of ischemia decreased infarction size to 19% of the risk zone. While the protection observed with post-treatment was not as great as that observed with pre-treatment, the infarction was still 43% smaller than the infarction in untreated hearts. Thus, administration of fostriecin, even after the infarction episode, provides an advantage over the preconditioning mimetics currently known (e.g. adenosine or phenyleprine), none of which is capable of providing protection when administered post-infarction. Furthermore, rabbits have a very sparse collateral circulation. Thus the ability of a drug to enter the tissue "downstream" of the occlusion is more limited in a rabbit than in a human. This makes the results obtained with the method of the present invention even more remarkable.

EXAMPLE 7

Fostriecin has Protective Effects in an Isolated Myocyte Cell Model System

The isolated myocyte assay measures the appearance of osmotic fragility which occurs during ischemia, employing a fragility index based on the area under a curve where the percentage of trypan blue-positive myocytes is plotted against time (see Armstrong, et al., Cardiovasc. Res. 28:1049–56 (1994)). When 10 μM fostriecin was added to cells at the onset of ischemia, a significant reduction in cell fragility was observed (curve (10.6%•hr vs. 14.3%•hr in untreated cells at 120 min). This is on equal terms with the results obtained with ischemic preconditioning in this assay (FIG. 3).

EXAMPLE 8

Fostriecin has Potent Inhibitory Activity Against Certain Serine/Threonine Protein Phosphatases As seen in FIG. 4, the purified catalytic subunits of both PP1 and PP2A are inhibited by fostriecin in a dose-dependent manner. Similarly, fostriecin inhibits the divalent cation-independent serine/threonine protein phosphatase activity contained in crude whole cell homogenates of rabbit heart ventricles (FIG. 5). The dephosphorylation of phosphohistone and phosphorylase-a by the purified catalytic subunits of both PP1 and PP2A is inhibited by fostriecin in a dose-dependent manner. Phosphatase activity was determined using [$^{32}$P]-labeled phosphoprotein substrates as described in Example 2, and fostriecin inhibits the activity of PP2A at a lower concentration than PP1. Similarly, fostriecin inhibits the divalent cation-independent serine/threonine protein phosphatase activity contained in crude whole cell homogenates of rabbit heart ventricles (FIG. 5).

In the studies depicted in FIG. 5, biopsies from the left ventricle were removed, weighed and homogenized in ice cold Tris buffer (50 mM Tris-base, pH 7.4 containing 1 mM EDTA). The homogenate was then subjected to centrifugation at 13,000×g for 10 minutes and the supernatant was removed. Aliquots of the supernatant were assayed for protein phosphatase activity using the same methodology employed with the purified catalytic subunits of PP1 and PP2A. With both the purified catalytic subunits and the dilute whole cell homogenate, the protective effect of fostriecin correlates well. Further, the protective effect of fostriecin correlates well with the inhibition of protein phosphatase activity. In rabbits, a concentration of 1–10 $\mu$M was found to provide protection. At this concentration, fostriecin inhibits PP2A completely, and has a minor effect on PP1 (FIG. 4). It should be noted, however, that though this concentration was effective for perfused hearts in rabbits, in whole blood concentrations will likely be higher.

EXAMPLE 9

To study the effects of fostriecin in more detail, PP2A from bovine brain and three isoforms of human PP1—alpha, beta and gamma—were cloned and sequenced. A chimera then was produced which contained the C-terminal domain of PP2A and the N-terminal domain of PP1-alpha (FIG. 6).

In these studies, the bacterial expressed PP1/PP2A hybrid enzyme was produced by growing appropriate strains of transformed *E. coli* at 18° C. for 48 hours in LB-media containing 50 $\mu$g/ml ampicillin, 1 mM MnCl$_2$, and 50 $\mu$M IPTG. The bacteria were lysed with a French Press, and after centrifugation at 15,000×g for 45 min, the phosphatase was partially purified via ion-exchange [High Q (BioRad) and MonoQ (Pharmacia)] and affinity [Heparin-Sepharose (Pharmacia)] chromatography. The sensitivity of the chimera to fostriecin was determined employing the same protein phosphatase assay employed with endogenous PP1 or PP2A, with the addition of MnCl$_2$ (1 mM) to the assay buffer. As seen in FIG. 7, the chimera is sensitive to fostriecin. However, since the potency of fostriecin inhibition for the chimera is similar to that of PP1 while the potency of inhibition of okadaic acid is similar to that of PP2A, it is likely that fostriecin and okadaic acid have different binding domains. In addition, the inhibition profile produced with fostriecin shown in FIG. 5 suggests that the heart homogenate contains more than two protein phosphatases that are sensitive to fostriecin.

To identify additional protein phosphatases that have structures similar to PP1 and PP2A, degenerate probes to regions conserved in both PP1 and PP2A were employed to screen a human cDNA library. In addition to PP1 and PP2A, two additional protein phosphatases were identified: PP4 and PP5. PP4 is approximately 65% homologous to PP2A, and the core region of PP5 is also highly homologous to PP2A. Northern analysis indicates that both PP4 and PP5 are present in heart, suggesting that they may also contribute to the fostriecin-sensitive protein phosphatase activity contained in the heart homogenate. Fostriecin had no effect on PP2B, alkaline protein phosphatase, acid phosphatase or a variety of protein kinases; and a comparison of the fostriecin-sensitive protein phosphatases indicate that they all contain the sequence RGNHE (SEQ ID NO.1).

To determine if preconditioning could produce changes in protein phosphatase activity, changes in protein phosphatase activity were assessed in crude whole-cell homogenates from heart biopsies which had undergone a 30-minute period of ischemia. The activity in the ischemic samples was then compared to protein phosphatase activity in biopsies of hearts preconditioned by a 5-minute period of ischemia. As seen in FIGS. 8A and 8B, an increase in okadaic acid resistant protein phosphatase activity (PP1, PP4 and/or PP5) was noted following reperfusion. Activity then declined rapidly during the 30 minute ischemic treatment; however, activity in preconditioned tissue remained higher for 20 minutes.

A model which reconciles the observed data is shown in FIG. 9. In normal tissue, the activity of PP1 and PP2A are regulated by regulatory proteins (Wera, et al., *Biochem. J.* 311:17–29 (1995)). For example, inhibitor 2 (I-2) decreases the activity of PP1 and the phosphorylated form of I-2 is a good substrate for PP2A. When I-2 is phosphorylated, it is degraded more rapidly, which results in a net increase in cellular PP1 activity. Thus, PP2A, by maintaining I-2 in an underphosphorylated state, inhibits the activity of PP1. According to this model, preconditioning could lead to the inactivation of PP2A—and possibly PP4 and PP5. Inactivation results in the hyperphosphorylation of I-2, causing its degradation. The net effect is an increase in PP1 activity, which provides the cells with protection via an unknown mechanism. When the cells are treated with fostriecin, the concentration that provides protection inhibits the activity of PP2A ( and possible PP4/PP5) but has no direct effect on PP1. Thus, fostriecin may mimic the events normally occurring during preconditioning. Alternatively, fostriecin may enhance the effects of protein kinase C via the inhibition of protein phosphatase activity that normally dephosphorylates enzymes phosphorylated by protein kinase C.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for treating an individual with cardiovascular disease, comprising the step of administering a therapeutically effective amount of fostriecin, an analog thereof, to said individual after the onset of cardiac ischemia.

2. The method of claim 1, wherein said individual is having a myocardial infarction.

3. The method of claim 2, further including the step of performing percutaneous transluminal coronary angioplasty on said individual.

4. The method of claim 2, further including the step of administering thrombolytic agents to said individual.

5. The method of claim 1, wherein said individual is susceptible to a myocardial infarction and said fostriecin is administered to said individual prior to said myocardial infarction.

6. The method of claim 5, further comprising the step of pharmacologically or mechanically preconditioning cardiac tissue of said individual.

7. The method of claim 5, further including the step of administering thrombolytic agents to said individual.

8. The method of claim 5, wherein said final concentration of said fostriecin after administration in infarcted tissue is about 0.1 $\mu$M to about 500 $\mu$M.

9. The method of claim 1, wherein said final concentration of said fostriecin in infarcted tissue after administration is about 0.1 $\mu$M to about 500 $\mu$M.

10. A method of screening for compounds effective in diminishing cardiac ischemia, comprising the steps of:

measuring an amount of phosphatase activity in a first sample of a purified catalytic subunit of a serine/threonine phosphatase to produce a control activity level;

measuring an amount of phosphatase activity in a second sample of a purified catalytic subunit of a serine/threonine phosphatase that has been treated with a compound to produce an experimental activity level; and comparing said control activity level to said experimental activity level, wherein said compound is effective in diminishing cardiac ischemia if said experimental activity level is lower than said control activity level.

11. The method of claim 10, wherein said purified catalytic subunit of a serine/threonine phosphatase is PP1.

12. The method of claim 10, wherein said purified catalytic subunit of a serine/threonine phosphatase is PP2A.

13. A method of screening for compounds effective in diminishing cardiac ischemia, comprising the steps of:

measuring an amount of divalent cation-independent phosphatase activity in a first sample of a whole cell ventricle homogenate to produce a control activity level;

measuring an amount of divalent cation-independent phosphatase activity in a second sample of a whole cell ventricle homogenate that has been treated with a compound to produce an experimental activity level; and comparing said control activity level to said experimental activity level, wherein said compound is effective in diminishing cardiac ischemia if said experimental activity level is lower than said control activity level.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 5 amino acids
      (B) TYPE: amino acid
      (D) TOPOLOGY: linear (ii) MOLECULE TYPE:
      (A) DESCRIPTION: protein (iii) HYPOTHETICAL: no (iv) ANTI-SENSE: no (v) FRAGMENT TYPE: internal (xi) SEQUENCE DESCRIPTION:SEQ ID NO: 1:

Arg Gly Asn His Glu